(12) United States Patent  
Ootomo (10) Patent No.: US 6,269,261 B1  
(45) Date of Patent: Jul. 31, 2001

(54) HEALTH CARE INSTRUMENT CONTAINING OXIDATION-REDUCTION POTENTIAL MEASURING FUNCTION

(75) Inventor: Yoshitaka Ootomo, Fujisawa (JP)

(73) Assignee: Yugen Kaisha Endo Process, Tokyo (JP)

( * ) Notice: Subject to any disclaimer, the term of this patent is extended or adjusted under 35 U.S.C. 154(b) by 0 days.

(21) Appl. No.: 08/957,553

(22) Filed: Oct. 24, 1997

(30) Foreign Application Priority Data

Oct. 26, 1996 (JP) .................................................. 8-320662

(51) Int. Cl.$^7$ ...................................................... A61B 5/05
(52) U.S. Cl. ........................ 600/345; 600/346; 600/349; 600/355; 600/573; 600/584
(58) Field of Search ................... 600/345–351, 600/353, 355, 364–365, 547, 551, 584, 357, 573

(56) References Cited

U.S. PATENT DOCUMENTS

| | | | |
|---|---|---|---|
| 4,637,403 | * | 1/1987 | Garcia et al. ..................... 600/345 X |
| 4,753,247 | * | 6/1988 | Kirsner .............................. 600/345 X |
| 4,805,624 | * | 2/1989 | Yao et al. .......................... 600/345 X |

* cited by examiner

Primary Examiner—Cary O'Connor  
Assistant Examiner—Ryan Carter  
(74) Attorney, Agent, or Firm—Ladas & Parry

(57) ABSTRACT

The invention aims to provide a health care instrument adapted to measure oxidation-reduction potential in human being, animal, fish and shellfish, plant, vegetable as well as water, air or earth surrounding those organisms and thereby to determine a level of active oxygen in such subject so that the measured data may be used for health care. The object set forth above is achieved by a health care instrument containing an oxidation-reduction potential measuring function comprising a main body, a power source consisting of a battery with or without a battery charger and an oxidation-reduction potential measuring unit both contained in the main body, a measuring probe attached to one end of the main body, a sensor included in the measure probe so as to be connected to the oxidation-reduction potential measuring unit, and a display unit provided on a part of the main body to display the measured oxidation-reduction potential value. The health care instrument according to the invention allows the oxidation-reduction potential in the subject to be easily determined in order to know a condition of the subject's health or growth. The health care instrument allows an internal abnormal condition to be detected and thereby allows the subject to be prevented from being affected by disease. Thus, the health care instrument according to the invention effectively contributes to health care.

69 Claims, 4 Drawing Sheets

HEALTH CARE INSTRUMENT CONTAINING OXIDATION-REDUCTION POTENTIAL MEASURING FUNCTION

BACKGROUND OF THE INVENTION

1. Field of the Invention

The present invention relates to a health care instrument used to measure internal oxidation-reduction potential of animated things such as a human being, an animal, fish and shellfish or plants and thereby to determine a condition of internal active oxygen.

2. Description of the Related Art

In the case of a human being, if an abnormal physical condition is suspected on the basis of a change in physical condition, the condition of health is often experientially determined by measuring his or her bodily temperature and comparing the measured temperature with his or her normal bodily temperature. The person then may seek medical advice from a doctor. However, this is a countermeasure taken after particular symptoms have appeared and such countermeasure is often too late to achieve health recovery.

Recently, the active oxygen has been reported as one of the important factors inducing diseases, for example, by Tokyo National Preventology Institute.

Oxygen is essential to animals including human beings and it is this oxygen that causes combustion in the body for generation of heat and energy. However, the oxygen is liable to be bonded to the surrounding substances in the form of hydrogen bond, covalent bond, ionic bond etc. The oxygen atom is bonded to the surrounding other atoms to form a molecule which is stable so long as this molecule has eight outer electrons. If the number of these outer electrons is insufficient, the oxygen atom tends to be bonded to the neighboring substances. The oxygen in such condition has an oxidizing ability higher than the oxygen in normal condition. Such oxygen is referred to as active oxygen and it has already been found that the active oxygen often threatens a person's health when it is bonded to an unsaturated fatty acid in the body to produce lipid peroxide.

The cells in a person's body are protected by the cell walls. These cell walls function to receive the nutrients and produce the biological active substances essential to the human body. However, the active oxygen readily destroys these cell walls and consequently the cell walls not only lose their proper function but also these destroyed cell walls produce the substances injuring the rest of the healthy cells, inducing various diseases.

On the other hand, various external factors such as air pollution due to destroyed natural environment, vegetables having residual pesticide, and chemically processed products have recently caused the environment polluting substances to enter the human body. In addition, the psychogenic factors cause the internal stresses. These factors have seriously injured our health. While the active oxygen is produced in the body to remove such environment pulluting substances and thereby to maintain the health, excessively produced active oxygen (excessive active oxygen) destroys even the healthy cells, as has previously described, and causes various diseases.

If generation of the active oxygen functioning to destroy even the healthy cells can be quickly detected, such detection will effectively contribute to maintain the health. The inventor has noticed that the active oxygen (excessive active oxygen) readily induces various diseases; and he aims to provide an instrument allowing oxidation-reduction potential in the body to be measured by an individual him- or herself in order to determine his or her physical condition, based on which said active oxygen (excessive active oxygen) is reduced to achieve the desired health care.

Introduction of a platinum electrode and hydrogen electrode into solution containing an oxidation-reduction couple generates a potential between these electrodes. Such potential is referred to as Oxidation Reduction Potential, (abbreviated as ORP). ORP is defined as follows:

$$E = E_0 + \frac{RT}{nF} \ln \frac{[Ox]}{[Red]}$$

where
- E: oxidation-reduction potential (V)
- $E_0$: reference oxidation-reduction potential (V)
- R: gas constant
- T: absolute temperature
- n: ionic charge number
- F: Faraday constant
- [Ox]: oxidizer concentration (mol/l)
- [Red]: reducer concentration (mol/l)
- $E_0$ corresponds to E when [Ox]=[Red] and a constant for the relevant system.

According to the definition, two substances should be limited to those having electrons reversibly increasing and decreasing as the electrons transfer. The potential to be measured must be that in equilibrium under a certain environment. Since the potential is measured as that between two substances, the substance having larger number of electrons lies on minus side and the substance having smaller number of electrons lies on plus side. The invention is based on the fact that the ORP value corresponds to a mixed potential represented by a weighted average obtained from reaction energies of all ions and molecules even in body fluids of animals as well as plants containing biologically active substances such as enzymes: and such mixed potential can be used for measuring oxidation-reduction potential not only in a human body but also in animals and plants.

Condition of the active oxygen in the body can be determined by measuring the oxidation-reduction potential in the body. The interior of the healthy human body is maintained in an alkaline condition and thereby the health is maintained by the natural curative processes. On the contrary, exterior of the human body is in an acid condition. The previously mentioned oxidation-reduction potential (mV) is an index of ability with which a compound oxidizes or reduces the other compound. The compound having a higher plus value of the oxidation-reduction potential exhibits a correspondingly higher oxidizing ability (i.e., highly corrosive), and the compound having a lower minus value of the oxidation-reduction potential exhibits a correspondingly higher reducing ability (i.e., beneficial for the health). Transfer of electrons and reaction of energy metabolism occurring in all living matters are oxidation-reduction reactions: and it is very important to measure the oxidation-reduction potential value in the body to maintain the living matters in healthy condition.

It is important to ingest the foods having high minus values of oxidation-reduction potential and functioning as substance scavengers which add the active oxygen with additional electrons for reduction effect. It is also important to eliminate the stresses tending to induce such stresses. To establish the eating habits allowing the oxidation-reduction potential to be maintained at a minus value, various foods including water, fruits, fishes and shellfishes may be taken on the basis of the oxidation-reduction potential values previously measured on these foods. In this manner, an effective counterplan against diseases can be considered in advance and the health can be consciously maintained.

The measured value of oxidation-reduction potential significantly lying on the plus side suggests that the physical condition is in an undesirable condition in a human body as well as in the other living matters such as animals, fishes, shellfishes and plants.

SUMMARY OF THE INVENTION

The present invention relates to a health care instrument containing an oxidation-reduction potential measuring function, said instrument comprising a main body, a power source consisting of a battery with or without a battery charger and an oxidation-reduction potential measuring unit both contained in said main body, a measuring probe attached to one end of said main body and including a sensor so as to be connected to said oxidation-reduction potential measuring unit, and a display unit provided on a part of said main body to display the measured oxidation-reduction potential value.

Preferably, said oxidation-reduction potential measuring unit comprises an oxidation-reduction potential detector, an oxidation-reduction potential decision circuit, a delay circuit, a measured oxidation-reduction potential value display unit, a switching circuit and an acoustic decision mechanism for measured oxidation-reduction potential value.

Preferably, said measuring probe is detachably and exchangeably mounted on the main body.

Preferably, the main body is partially provided with projections and/or clip.

Preferably, the instrument further comprises a memory mechanism functioning to store, reproduce and delete the measured oxidation-reduction potential value.

Preferably, said measured oxidation-reduction potential value display unit includes one or more of digital display, color display depending on the level of the measure value and audio display.

Preferably, said measured oxidation-reduction potential value display unit displays a health standard associated with said measured value.

DETAILED DESCRIPTION OF THE PREFERRED EMBODIMENTS

Figure 1:
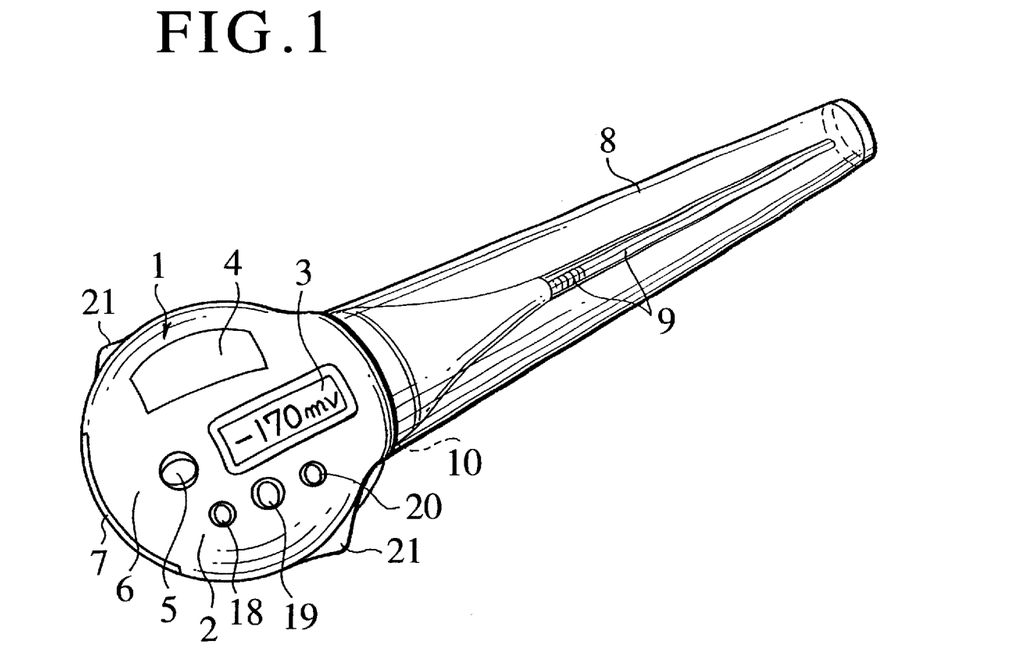
FIG. 1 is a perspective view illustrating an embodiment of the invention.
Figure 2:
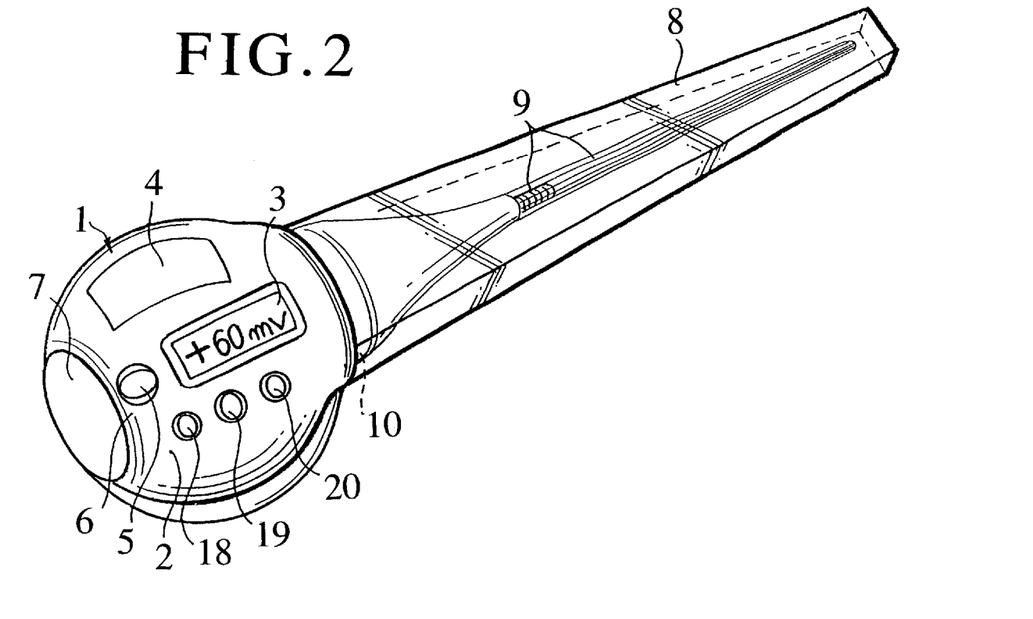
FIG. 2 is a view similar to FIG. 1 illustrating another embodiment of the invention.
Figure 3:
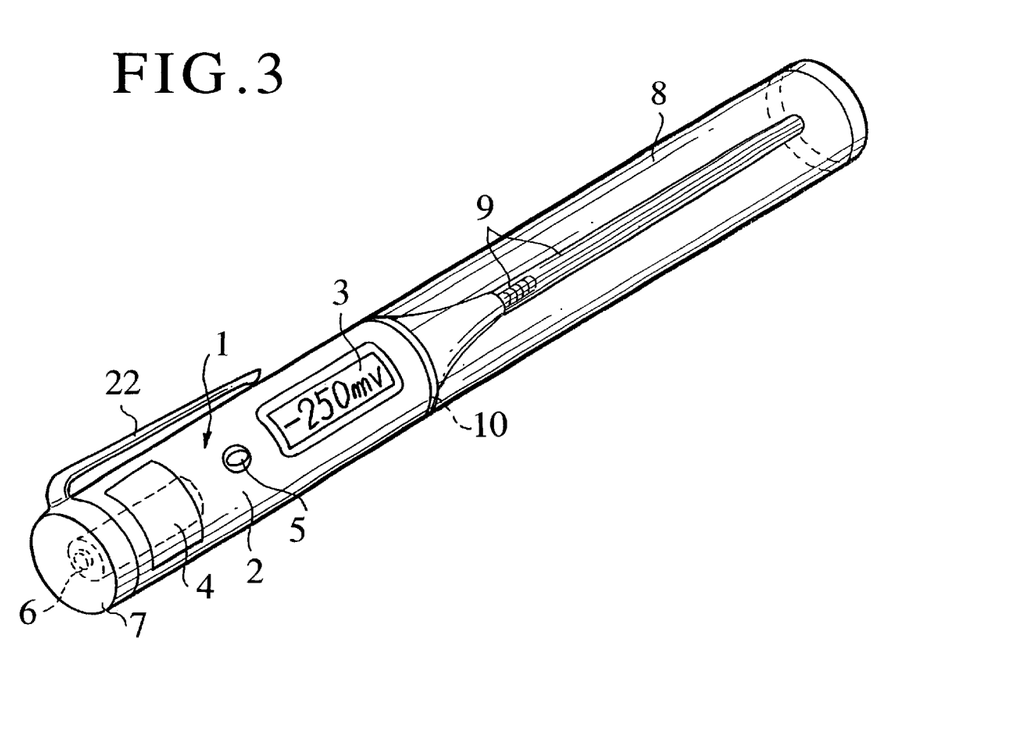
FIG. 3 is a view similar to FIG. 1 illustrating still another embodiment of the invention.
Figure 4:
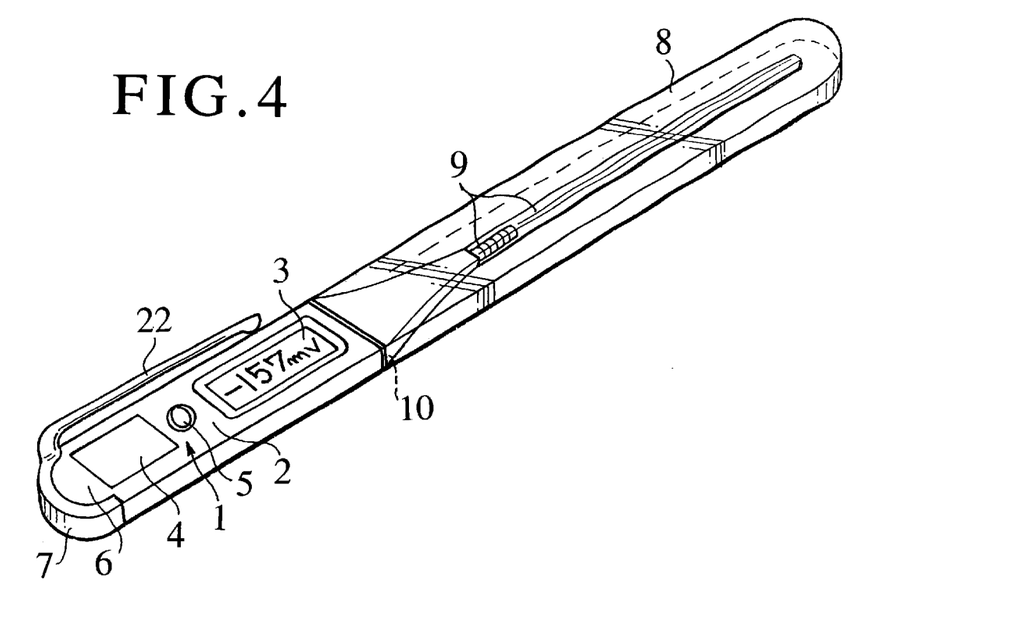
FIG. 4 is a view similar to FIG. 1 illustrating further another embodiment of the invention.
Figure 5:
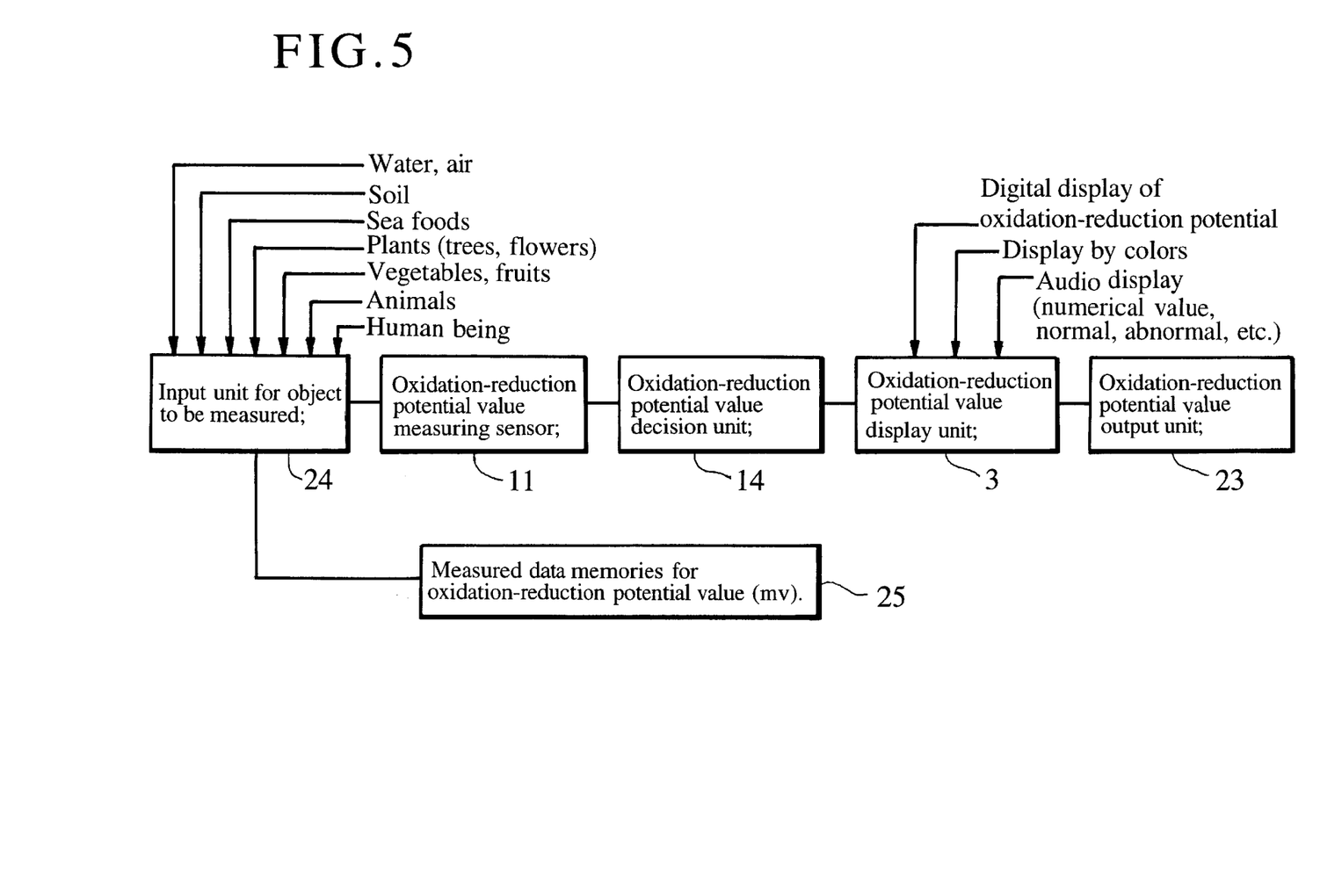
FIG. 5 is a block diagram illustrating a measuring system according to the invention.
Figure 6:
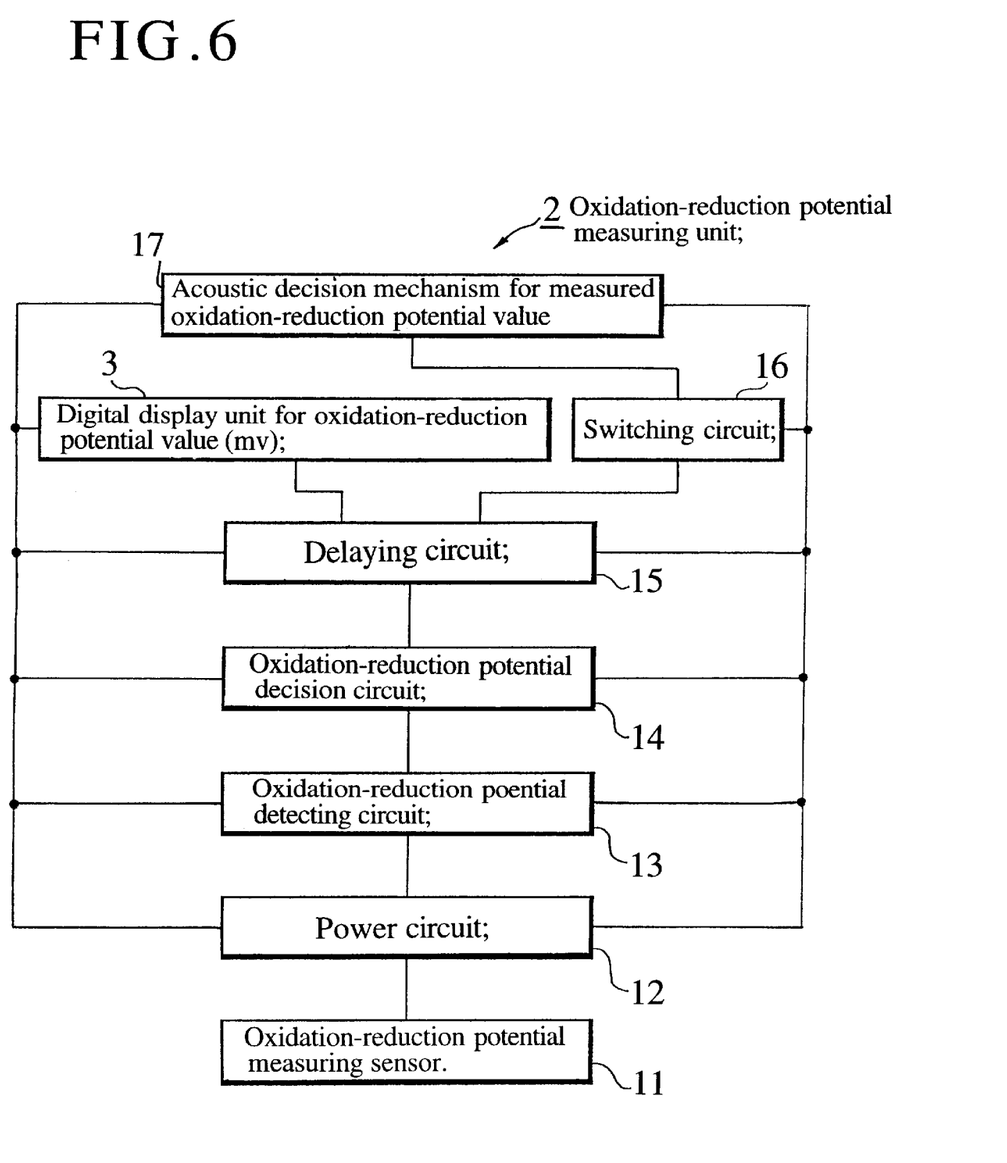
FIG. 6 is a diagram systematically illustrating an oxidation-reduction potential measuring unit adopted by the invention.

Details of the invention will be more fully understood from the description given hereunder in reference with the accompanying drawings. FIGS. 1 through 4 are perspective views illustrating specific embodiments of the invention. More particularly, FIG. 1 illustrates an embodiment of the invention comprising a spherical main body having projections formed on its spherical surface by which the instrument is prevented from rolling about and a casing tapered toward an end opposite to said main body so as to have a circular cross-section. FIG. 2 illustrates another embodiment of the invention having a flat configuration on the whole. FIG. 3 illustrates still another embodiment of the invention having a cylindrical configuration on the whole in which said main body is provided with a clip. FIG. 4 illustrates further another embodiment of the invention having a flat configuration on the whole in which said main body is provided with the clip as in the embodiment illustrated by FIG. 3. FIG. 5 is a block diagram illustrating a measuring system according to the invention. Finally, FIG. 6 is a system diagram illustrating the inventive instrument for measuring oxidation-reduction potential. Referring now to FIGS. 1 through 4, reference numeral 1 designates a main body containing therein an oxidation-reduction potential measuring unit 2 and a power source 6 comprising a battery optionally inclusive of auxiliary means such as a battery charger. One end of the main body 1 is tapered toward its distal end at which a measuring probe 9 is detachably mounted on said main body 1 and said measuring chamber 9 contains therein a measuring sensor 11 connected to said oxidation-reduction potential measuring unit 2. The main body 1 is provided on its surface with various means such as a measured value display 3 associated with said oxidation-reduction potential measuring unit 2, a health standard list 4 based on the measured oxidation-reduction potential value, a source switch 5, a data memory key 19 and a memory data deletion key 20. Reference numeral 7 designates a cover of the power source 6, and reference numeral 8 designates a casing adapted to be detachably attached to the main body 1 with one touch in order to cover/protect said sensor 9. Reference numeral 10 designates a mount for said casing 8, reference numeral 21 designates projections provided on the spherical surface of said main body so as to prevent said main body from rolling about and reference numeral 22 designates a clip provided on said main body 1.

Referring to FIG. 5 which illustrates the measuring system according to the invention, reference numeral 23 designates an output for the measured oxidation-reduction potential value, reference numeral 24 designates an input unit for the object to be measured and reference numeral 25 designates a measured data memory. Referring to FIG. 6 which systematically illustrates the oxidation-reduction potential measuring unit 2, reference numeral 11 designates a measuring sensor, reference numeral 12 designates a power circuit essentially comprising the power source 6, reference numeral 13 designates an oxidation-reduction potential detector, reference numeral 14 designates a decision circuit for oxidation-reduction potential, reference numeral 15 designates a delay circuit, reference numeral 3 designates an oxidation-reduction potential value display unit, reference numeral 16 designates a switching circuit and reference numeral 17 designates an acoustic decision mechanism for measured oxidation-reduction potential value.

The inventive instrument constructed as has been described hereinabove operates as follows: To measure an oxidation-reduction potential in the human body, the cover 7 is removed from the main body 1, the power source 6 is loaded with a battery or a battery previously contained in the power source 6 is charged so that the oxidation-reduction potential unit 2 can be ready for operation. Then, the casing 8 which has covered and protected the measuring probe 9 attached to the main body 1 is onetouch-detached from the mount 10 and thereby said measuring probe 9 is exposed. Now a subject holds said measuring portion 9 in his or her mouth with the measuring sensor 11 being partially placed on his or her tongue or with said measuring sensor 11 being licked and clamps his or her lips together for approximately 30 seconds. In this way, the internal oxidation-reduction potential value (mV) is determined.

The above-mentioned manner in which the instrument operates will be described more in detail with reference to FIG. 6. A detection signal output from the measuring sensor 11 is applied through the oxidation-reduction potential detector 13 to the oxidation-reduction potential value determining circuit 14 by which the oxidation-reduction potential value is determined. An actuation signal is applied from said circuit 14 to the delay circuit 15 which delays said signal for a predetermined period to determine whether the applied signal is a noise or not: and, after said signal has been determined to be the correct measurement signal, transmits said signal to the switching circuit 16 and the measured oxidation-reduction potential value display unit 3. In response to said signal, the measured oxidation-reduction potential value display unit 3 digitally displays this measured value. The switching circuit 16, on the other hand, is responsive to said signal to actuate the acoustic decision mechanism for measured oxidation-reduction potential value 17 to generate sound indicating completion of the measurement. A subject may compare the value displayed on the measured oxidation-reduction potential value display unit with the health standard list 4 provided on the spherical surface of the main body 1 to be informed of his or her own health condition. The measurement data may be displayed by means of various display techniques such as digital display, color display depending on a level of the measured value or audio display.

Upon completion of the measurement, the power switch 5 is turned off and the casing 8 is reattached to the main body 1 to cover the measuring probe 9. Then, the data memory key 18 arranged on the spherical surface of the main body 1 is operated to store the measured data into the data memory 25. If necessary, the data call key 19 may be operated to read out the data from the measured data memory 25; and these read-out data may be reproduced to be compared with the other measured data. If the data stored in said measured data memory 25 becomes unnecessary, such data may be deleted by operating the memory data deletion key 20.

It is also possible to provide said measured data memory 25 externally of the main body 1 and may be connected to the main body 1 whenever it is necessary.

After completion of measurement, the measuring probe 9 may be removed from the main body 1 and may be exchanged with a fresh probe. Such a feature is preferable from the viewpoint of the sanitary security since infection is due to body fluids, for example, saliva of the other subjects.

Measurement of oxidation-reduction potential value in the human body can be achieved not also in the mouth but also based on body fluids such as saliva; perspiration on the palm, the axilla or the hair; or urine or blood.

As will be apparent from FIGS. 1 through 4, the inventive instrument may have optionally various configurations such as spherical, cylindrical or flat configuration. For example, FIG. 1 illustrates an embodiment of the invention comprising the spherical main body having projections formed on its spherical surface by which the instrument is prevented from rolling about and a casing tapered toward an end opposite to said main body so as to have a circular cross-section, FIG. 2 illustrates another embodiment of the invention having a flat configuration on the whole, FIG. 3 illustrates still another embodiment of the invention having a cylindrical configuration on the whole in which said main body is provided with a clip, and FIG. 4 illustrates further another embodiment of the invention having a flat configuration on the whole in which said main body is provided with the clip. To prevent the instrument from rolling about, said projections 21 or clip 22 provided on the main body 1 are effective.

EXAMPLE

On healthy and unhealthy subjects, the inventor measured oxidation-reduction potential (mV) by using the inventive instrument and obtained the result as shown in TABLE 1:

TABLE 1

| Subjects | mV | Health analysis by subjects themselves |
|---|---|---|
| Group A | −190 | Satisfactory physical condition and confidence in his or her own health. |
| Group B | −157 | Constant body weight and full vitality. |
| Group C | −50 | Though hardly conscious of it, health standard is not met. |
| Group D | +72 | Liable to catch cold but no subjective symptoms such as pain. |
| Group E | +120 | Liable to catch cold but none of serious diseases requiring the subject to enter hospital |
| Group F | +200 | Somewhat conscious of suspenseful physical condition as well as subjective symptoms and liable to be tired. |
| Group G | +280 | Going to hospital regularly with subjective symptoms and apprehension about health. |
| Group H | +350 | Repeatedly entering and leaving hospital, feeling regret for health care. |

The measurement was carried out on Groups A~H each consisting of 10~15 subjects. It should be understood that the oxidation-reduction potential values (mV) for the respective Groups represent averages of the oxidation-reduction potential values obtained on the subjects belonging to the respective Groups.

From the ORP values shown in TABLE 1 which were obtained in the outpatient clinic on the respective Groups A~H by using the inventive health care instrument containing the oxidation-reduction potential value measuring function, the following tendency was discovered: Many patients suffering from lung cancer, gastric cancer and liver cancer were found in Groups F and G and the average ORP value determined on these Groups was in a range of +200~+280. It was also discovered that many patients suffering from hepatitis C, hypertension, diabetes, hepatopathy, cystitis, cecitis, Behcet's syndrome, asthmatic fit and collagenosis were found in Groups D and E and the average ORP value determined on these Groups was in a range of +72~ +120. The healthy subjects having neither experience of going to hospital regularly nor subjective symptoms and being problemless in complexion, appetite, vitality and physical stamina were found in Groups A, B, C and the average ORP value determined on these Groups was in a range of −50~−190.

As will be apparent from such result of measurement, for the Group H of subjects who are entering and leaving hospital repeatedly, the average oxidation-reduction potential value of +350 was recorded. On the other hand, the average oxidation-reduction potential value of −190 was recorded for the Group A of subjects who are very healthy. A difference between these two average potential values is as large as 540. The result obtained from sufficiently many subjects evidently suggests that a large difference in the measured values appears between the healthy subjects and the unhealthy subjects. It was also found that larger the minus value of the oxidation-reduction potential, the higher the consciousness and confidence in the health: and larger the plus value of the oxidation-reduction potential, the more significant the subjective symptoms and the apprehension about health.

Accordingly, it is possible for the subject having exhibited a plus value of the oxidation-reduction potential to improve the oxidation-reduction potential value and thereby to achieve health recovery by taking an appropriate remedy such as improvement of his or her diet or removal of stress factor and to avoid being affected by a disease.

As in the case of a human being, the invention can be used to determine oxidation-reduction potential value in an animal by causing the animal to hold the measuring probe 9 in his or her lips.

Also for a fish or shellfish or plant, the measuring probe 9 may be directly inserted into the fish or shellfish to measure the oxidation-reduction potential value: or after said plant has been immersed into water, the oxidation-reduction potential value of this water may be measured.

In view of the fact that withering of trees due to acid rain has recently become serious, the instrument according to the invention can be used to determine a condition of their growth. More specifically, a sufficiently small hole to maintain its growth may be made in its trunks; and the measuring probe 9 may be inserted into this hole.

As will be understood from the foregoing description, the invention allows the internal oxidation-reduction potential value of animated beings such as human beings to be measured and thereby allows a condition of health to be determined. In this way, the invention allows an abnormal condition in the body and thereby allows affliction by a disease to be avoided. Further it will be possible to take proper measures for an operation by monitoring measured oxidation-reduction potential value changing in the progress of performing the operation The invention uses no chemicals and very small electric current so that the measuring probe may be held in lips without danger. The inventive instrument is convenient for health care since even the aged as well as the children can use the inventive instrument without any anxiety.

Furthermore, the measuring probe containing therein the measuring sensor is detachably mounted on the main body and can be exchanged with a fresh measuring probe after it has been used. Accordingly, the instrument can be used without any anxiety because there is no apprehension that the infection might occur due to the measuring probe having been used by the other person.

The invention is applicable not only to measurement of oxidation-reduction potential value in human being but also to such measurement in animals, fishes or shellfishes, plants, vegetables and fruits in order to determine their health, growth or freshness. Additionally, the invention is applicable to measurement of oxidation-reduction potential value in water, air and earth constituting the environment in which said various subjects live.

What is claimed is:

1. A health-care instrument comprising:
   (a) a sensor for measuring an oxidation-reduction potential value, wherein the sensor produces a detection signal output;
   (b) a circuit for determining the oxidation-reduction potential value from the detection signal output, wherein the circuit produces an actuation signal;
   (c) a delay circuit that delays the actuation signal for a period of time to determine whether the actuation signal is noise, wherein, if the actuation signal is not noise, the actuation signal is transmitted to a display unit; and wherein the actuation signal causes the display unit to display the oxidation-reduction potential value.

2. A health-care instrument as claimed in claim 1, wherein the sensor measures the oxidation-reduction potential value of a fluid obtained from a subject, wherein the instrument further comprises a main body connected to the sensor and a health-standard list on the main body, and wherein the health-standard list shows how the oxidation-reduction potential value correlates with health of the subject.

3. A health-care instrument as claimed in claim 2, wherein the health-standard list indicates that the subject is healthy if the oxidation-reduction potential value is less than −50 mV.

4. A health-care instrument as claimed in claim 2, wherein the health-standard list indicates that the subject is not healthy if the oxidation-reduction potential value is greater than or equal to 72 mV.

5. A health-care instrument as claimed in claim 1, wherein the sensor measures the oxidation-reduction potential value of a fluid obtained from a subject, and wherein the display unit also displays how the oxidation-reduction potential value correlates with health of the subject.

6. A health-care instrument as claimed in claim 5, wherein the display unit indicates that the subject is healthy if the oxidation-reduction potential value is less than −50 mV.

7. A health-care instrument as claimed in claim 5, wherein the display unit indicates that the subject is not healthy if the oxidation-reduction potential value is greater than or equal to 72 mV.

8. A health-care instrument comprising:
   (a) a means for measuring an oxidation-reduction potential value, wherein the measuring means produces a detection signal output;
   (b) a means for determining the oxidation-reduction potential value from the detection signal output, wherein the determining means produces an actuation signal;
   (c) a means for delaying the actuation signal for a period of time to determine whether the actuation signal is noise, wherein, if the actuation signal is not noise, the actuation signal is transmitted to a display means; and wherein the actuation signal causes the display means to display the oxidation-reduction potential value.

9. A health-care instrument as claimed in claim 8, wherein the sensor measures the oxidation-reduction potential value of a fluid obtained from a subject, and wherein the display means also displays how the oxidation-reduction potential value correlates with health of the subject.

10. A health-care instrument as claimed in claim 8, further comprising a memory mechanism for storing, reproducing, and/or deleting the oxidation-reduction potential value measured by the sensor.

11. A health-care instrument as claimed in claim 9, wherein the display means indicates that the subject is healthy if the oxidation-reduction potential value is less than −50 mV.

12. A health-care instrument as claimed in claim 9, wherein the display means indicates that the subject is not healthy if the oxidation-reduction potential value is greater than or equal to 72 mV.

13. A health-care instrument as claimed in claim 1, wherein the instrument includes a probe and a main body, wherein the probe comprises the sensor, and wherein the probe is detachably and/or exchangeably mounted on the main body.

14. A health-care instrument as claimed in claim 1, further comprising a memory mechanism for storing, reproducing, and/or deleting the oxidation-reduction potential value measured by the sensor.

15. A health-care instrument as claimed in claim 14, wherein a data memory key controls whether the oxidation-reduction potential value is stored in the memory mechanism.

16. A health-care instrument as claimed in claim 14, wherein a data call key controls whether datum stored in the memory mechanism is read out from the memory mechanism.

17. A health-care instrument as claimed in claim 14, wherein a data deletion key controls whether datum stored in the memory mechanism is deleted from the memory mechanism.

18. A health-care instrument as claimed in claim 1, wherein the instrument includes a main body connected to the sensor, wherein the main body is flat or is partially provided with a projection and/or a clip.

19. A health-care instrument as claimed in claim 1, wherein the sensor measures the oxidation-reduction potential value of a fluid, wherein the fluid comprises saliva, sweat, urine, or blood; and wherein the oxidation-reduction potential value of the fluid is measured when the sensor is brought into contact with the fluid.

20. A health-care instrument as claimed in claim 1, wherein the display unit includes one or more of a digital display, a color display, and an audio display, wherein the digital display, color display, and/or audio display depend on the oxidation-reduction potential value measured by the sensor.

21. A health-care instrument as claimed in claim 1, wherein the sensor measures the oxidation-reduction potential value of a fluid obtained from a subject; and wherein the subject is a human being, an animal, a fish, a shellfish, a plant, a vegetable, or a fruit.

22. A health-care instrument as claimed in claim 1, wherein the instrument further comprises an acoustic mechanism, wherein, if the actuation signal is not noise, the actuation signal causes the acoustic mechanism to generate a sound indicating that the oxidation-reduction potential value has been measured.

23. A health-care instrument as claimed in claim 22, wherein the sensor measures the oxidation-reduction potential value of a fluid obtained from a subject, and wherein the display unit also displays how the oxidation-reduction potential value correlates with health of the subject.

24. A health-care instrument as claimed in claim 22, further comprising a memory mechanism for storing, reproducing, and/or deleting the oxidation-reduction potential value measured by the sensor.

25. A health-care instrument as claimed in claim 8, wherein the sensor measures the oxidation-reduction potential value of a fluid obtained from a subject, wherein the instrument further comprises a main body connected to the sensor and a health-standard list on the main body, wherein the health-standard list shows how the oxidation-reduction potential value correlates with health of the subject.

26. A health-care instrument as claimed in claim 25, wherein the health-standard list indicates that the subject is healthy if the oxidation-reduction potential value is less than −50 mV.

27. A health-care instrument as claimed in claim 25, wherein the health-standard list indicates that the subject is not healthy if the oxidation-reduction potential value is greater than or equal to 72 mV.

28. A health-care instrument as claimed in claim 8, wherein the means for determining the oxidation-reduction potential value comprises an oxidation-reduction potential detector and an oxidation-reduction potential decision circuit.

29. A health-care instrument comprising:
   (a) a sensor for measuring an oxidation-reduction potential value of a fluid from a subject; and
   (b) a display unit to display the oxidation-reduction potential value measured by the sensor, wherein the display unit also displays how the oxidation-reduction potential value correlates with health of the subject.

30. A health-care instrument as claimed in claim 29, wherein the display unit indicates that the subject is healthy if the oxidation-reduction potential value is less than −50 mV.

31. A health-care instrument as claimed in claim 29, wherein the display unit indicates that the subject is not healthy if the oxidation-reduction potential value is greater than or equal to 72 mV.

32. A health-care instrument as claimed in claim 29, wherein the display unit indicates that the subject has cancer if the oxidation-reduction potential value is in a range of 200 to 280 mV.

33. A health-care instrument as claimed in claim 25, wherein the means for determining the oxidation-reduction potential value comprises an oxidation-reduction potential detector and an oxidation-reduction potential decision circuit.

34. A health-care instrument as claimed in claim 8, wherein the instrument further comprises an acoustic means, wherein, if the actuation signal is not noise, the actuation signal causes the acoustic means to generate a sound indicating that the oxidation-reduction potential value has been measured.

35. A health-care instrument as claimed in claim 34, wherein the means for determining the oxidation-reduction potential value comprises an oxidation-reduction potential detector and an oxidation-reduction potential decision circuit.

36. A health-care instrument as claimed in claim 34, wherein the sensor measures the oxidation-reduction potential value of a fluid obtained from a subject, and wherein the display means also displays how the oxidation-reduction potential value correlates with health of the subject.

37. A health-care instrument comprising:
   (a) a main body;
   (b) a sensor for measuring an oxidation-reduction potential value of a fluid from a subject, wherein the sensor is connected to the main body;
   (c) a display unit to display the oxidation-reduction potential value measured by the sensor; and
   (d) a health-standard list on the main body, wherein the health-standard list shows how the oxidation-reduction potential value correlates with health of the subject.

38. A health-care instrument as claimed in claim 37, wherein the health-standard list indicates that the subject is healthy if the oxidation-reduction potential value is less than −50 mV.

39. A health-care instrument as claimed in claim 37, wherein the health-standard list indicates that the subject is not healthy if the oxidation-reduction potential value is greater than or equal to 72 mV.

40. A health-care instrument as claimed in claim 37, wherein the health-standard list indicates that the subject has cancer if the oxidation-reduction potential value is in a range of 200 to 280 mV.

41. A health-care instrument comprising:
(a) a measuring means for measuring an oxidation-reduction potential value of fluid, wherein the measuring means comprises a probe; and
(b) a means for displaying the oxidation-reduction potential value measured by the measuring means;
wherein the probe comprises a sensor that produces a detection signal output, and wherein the instrument further comprises:
a circuit for determining the oxidation-reduction potential value from the detection signal output, wherein the circuit produces an actuation signal; and
a delay circuit that delays the actuation signal for a period of time to determine whether the actuation signal is noise, wherein, if the actuation signal is not noise, the actuation signal is transmitted to a display unit; and wherein the actuation signal causes the display unit to display the oxidation-reduction potential value.

42. A health-care instrument as claimed in claim 41, wherein the instrument further comprises an acoustic mechanism, wherein, if the actuation signal is not noise, the actuation signal causes the acoustic mechanism to generate a sound indicating that the oxidation-reduction potential value has been measured.

43. A health-care instrument comprising:
(a) a measuring means for measuring an oxidation-reduction potential value of a fluid, wherein the measuring means comprises a probe; and
(b) a means for displaying the oxidation-reduction potential value measured by the measuring means;
wherein the probe comprises a sensor that produces a detection signal output, and wherein the instrument further comprises:
a means for determining the oxidation-reduction potential value form the detection signal output, wherein the determining means produces an actuation signal;
a means for delaying the actuation signal for a period of time to determine whether the actuation signal is noise, wherein, if the actuation signal is not noise, the actuation signal is transmitted to a display means; and wherein the actuation signal causes the display means to display the oxidation-reduction potential value.

44. A health-care instrument as claimed in claim 43, wherein the instrument further comprises an acoustic means, wherein, if the actuation signal is not noise, the actuation signal causes the acoustic means to generate a sound indicating that the oxidation-reduction potential value has been measured.

45. A health-care instrument comprising:
(a) a measuring means for measuring an oxidation-reduction potential value of a fluid, wherein the measuring means comprises a probe; and
(b) a means for displaying the oxidation-reduction potential value measured by the measuring means;
wherein the fluid is obtained from a subject, wherein the instrument further comprises a main body connected to the probe and a health-standard list on the main body, and wherein the health-standard list shows how the oxidation-reduction potential value correlates with health of the subject.

46. A health-care instrument as claimed in claim 45, wherein the health-standard list indicates that the subject is healthy if the oxidation-reduction potential value is less than −50 mV.

47. A health-care instrument as claimed in claim 45, wherein the health-standard list indicates that the subject is not healthy if the oxidation-reduction potential value is greater than or equal to 72 mV.

48. A health-care instrument comprising:
(a) a measuring means for measuring an oxidation-reduction potential value of a fluid, wherein the measuring means comprises a probe; and
(b) a means for displaying the oxidation-reduction potential value measured by the measuring means;
wherein the fluid is obtained from a subject, and wherein the display unit also displays how the oxidation-reduction potential value correlates with health of the subject.

49. A health-care instrument as claimed in claim 48, wherein the display unit indicates that the subject is healthy if the oxidation-reduction potential value is less than −50 mV.

50. A health-care instrument as claimed in claim 48, wherein the display unit indicates that the subject is not healthy if the oxidation-reduction potential value is greater than or equal to 72 mV.

51. A method for determining health of a subject, the method comprising:
(1) measuring an oxidation-reduction potential value of a fluid from the subject;
(2) comparing the measured oxidation-reduction potential value with a health standard, wherein the health standard indicates how the oxidation-reduction potential value correlates with health of the subject.

52. A method as claimed in claim 51, wherein the health standard indicates that the subject is healthy if the oxidation-reduction potential value is less than −50 mV.

53. A method as claimed in claim 52, wherein the subject is a human being having a mouth and step (1) comprises placing a sensor in the mouth of the human being, wherein the sensor measures the oxidation-reduction potential value in the human being.

54. A method as claimed in claim 51, wherein the health standard indicates that the subject is not healthy if the oxidation-reduction potential value is greater than or equal to 72 mV.

55. A method as claimed in claim 55, wherein the subject is a human being having a mouth and step (1) comprises placing a sensor in the mouth of the human being, wherein the sensor measures the oxidation-reduction potential value in the human being.

56. A method as claimed in claim 51, wherein the health standard indicates that the subject has cancer if the oxidation-reduction potential value is in a range of 200 to 280 mV.

57. A method as claimed in claim 56, wherein the subject is a human being having a mouth and step (1) comprises placing a sensor in the mouth of the human being, wherein the sensor measures the oxidation-reduction potential value in the human being.

58. A method as claimed in claim 51, wherein the subject is a human being having a mouth and step (1) comprises placing a sensor in the mouth of the human being, wherein the sensor measures the oxidation-reduction potential value in the human being.

59. A method as claimed in claim 51, wherein the subject is a human being; and wherein the fluid comprises saliva, sweat, urine, or blood.

60. A method for determining if a subject is not healthy, the method comprising: measuring an oxidation-reduction potential value in a subject, wherein the subject is considered not healthy if the oxidation-reduction potential value is greater than or equal to 72 mV.

61. A method as claimed in claim 60, wherein the method indicates that the subject has cancer if the oxidation-reduction potential value is in a range of 200 to 280 mV.

62. A method as claimed in claim 60, wherein the subject is a human being having a mouth, and wherein measuring the oxidation-reduction potential value comprises placing a sensor in the mouth of the human being, wherein the sensor measures the oxidation-reduction potential value in the human being.

63. A method as claimed in claim 61, wherein the subject is a human being having a mouth, and wherein measuring the oxidation-reduction potential value comprises placing a sensor in the mouth of the human being, wherein the sensor measures the oxidation-reduction potential value in the human being.

64. A method as claimed in claim 60, wherein the method indicates that the subject has lung cancer, gastric cancer, or liver cancer if the oxidation-reduction potential value is in a range of 200 to 280 mV.

65. A method as claimed in claim 64, wherein the subject is a human being having a mouth, and wherein measuring the oxidation-reduction potential value comprises placing a sensor in the mouth of the human being, wherein the sensor measures the oxidation-reduction potential value in the human being.

66. A method as claimed in claim 60, wherein the method indicates that the subject has hepatitis, hypertension, diabetes, or asthma if the oxidation-reduction potential value is in a range of 72 to 120 mV.

67. A method as claimed in claim 66, wherein the subject is a human being having a mouth, and wherein measuring the oxidation-reduction potential value comprises placing a sensor in the mouth of the human being, wherein the sensor measures the oxidation-reduction potential value in the human being.

68. A method as claimed in claim 60, wherein the method indicates that the subject has hepatopathy, cystitis, cecitis, Behcet's syndrome, or collagenosis if the oxidation-reduction potential value is in a range of 72 to 120 mV.

69. A method as claimed in claim 68, wherein the subject is a human being having a mouth, and wherein measuring the oxidation-reduction potential value comprises placing a sensor in the mouth of the human being, wherein the sensor measures the oxidation-reduction potential value in the human being.

* * * * *